United States Patent [19]

Moore et al.

[11] 4,041,086

[45] * Aug. 9, 1977

[54] PROCESS OF MANUFACTURE OF FLOURINATED ALKYLADAMANTANES

[75] Inventors: Robert E. Moore, New Castle County, Del.; Edward J. Janoski, Havertown, Pa.

[73] Assignee: Sun Ventures, Inc., St. Davids, Pa.

[ * ] Notice: The portion of the term of this patent subsequent to Feb. 8, 1989, has been disclaimed.

[21] Appl. No.: 647,944

[22] Filed: Jan. 12, 1976

Related U.S. Application Data

[63] Continuation-in-part of Ser. No. 224,266, Feb. 7, 1972, abandoned, which is a continuation-in-part of Ser. No. 314,529, Oct. 7, 1963, abandoned, and Ser. No. 440,614, March 17, 1965, Pat. No. 3,641,167.

[51] Int. Cl.$^2$ .............................................. C07C 23/18
[52] U.S. Cl. ................................................ 260/648 F
[58] Field of Search .................................... 260/648 F

[56] References Cited

U.S. PATENT DOCUMENTS 3,641,167   2/1972   Moore et al. .................... 260/648 F

OTHER PUBLICATIONS

Chemical Abstracts, 85:142719v.
Chemical Abstracts, 85:934732.
Lovelace et al., Aliphatic Fluorine Compounds, pp. 10-12, (1958).
Stacey et al., Advances in Fluorine Chemistry, vol. 1, 166-175, 182-183, (1962).

Primary Examiner—Delbert E. Gantz
Assistant Examiner—J. Thierstein
Attorney, Agent, or Firm—J. Edward Hess; Donald R. Johnson; Stanford M. Back

[57] ABSTRACT

Novel, highly fluorinated hydrocarbons derived from the fluorination of alkyladamantanes, may be produced by known means, as for example by the process comprising contacting an alkyladamantane hydrocarbon, in vapor phase, with a fluoride of a transition metal (e.g., $CoF_3$, $MnF_3$, $AgF_2$) at 200°–400° C. The preferred adamantane hydrocarbons contain in the range of 11–30 (more preferred 12 to 14) carbon atoms and contain methyl and/or ethyl groups.

5 Claims, No Drawings

PROCESS OF MANUFACTURE OF FLOURINATED ALKYLADAMANTANES

CROSS REFERENCES TO RELATED APPLICATIONS

This application is a continuation-in-part of U.S. Ser. No. 224,266, filed Feb. 7, 1972, (now abandoned), which in turn is a continuation-in-part of copending applications Ser. No. 314,529, filed Oct. 7, 1963 (now abandoned) and Ser. No. 440,614, filed Mar.17, 1965 (now U.S. Pat. No. 3,641,167, issued Feb. 8, 1972).

Other related applications are the following:

| Serial No. | Filing Date | U.S. Pat. No. | Title/Inventor(s) |
|---|---|---|---|
| 679,801 | 11-1-67 | 3,597,358 (issued 8-3-71) | Traction Drive Transmission Containing Adamantanes pounds as Lubricants - IRL N. DULING-DAVID S. GATES-ROBERT E. MOORE-FREDERICK P. GLAZIER |
| 3,256 | 8-19-69 | 3,648,531 (issued 3-14-72) | Friction or Tractive Drive Fluid - IRL N. DULING-DAVID S. GATES-ROBERT E. MOORE-FREDERICK P. GLAZIER |
| 876,993 | 11-14-69 | 3,645,902 (issued 2-29-72) | Friction or Tractive Drive Fluid Comprising Adamantanes - IRL N. DULING-FREDERICK P. GLAZIER-DAVID S. GATES-ROBERT E. MOORE |
| 165,418 | 7-15-71 | 3,966,624 (issued 6-29-76) | Blended Traction Fluid Containing Hydrogenated Polyolefin - IRL N. DULING-DAVID S. GATES-FREDERICK P. GLAZIER-ROBERT E. MOORE-THOMAS D. NEWINGHAM |

The disclosure of all of the above cited applications is hereby incorporated herein by reference.

The Duling et al applications described the use of the process of the present invention to prepare fluoro and perfluoro derivatives of adamantane hydrocarbons of the $C_{10}$–$C_{30}$ range, and/or disclose that such fluorinated adamantanes are useful as traction fluids (or as components of blended traction fluids).

BACKGROUND OF THE INVENTION

This invention is directed to novel, highly fluorinated hydrocarbons, including perfluorinated hydrocarbons, obtained by the fluorination of alkyladamantane, particularly alkyladamantanes having from 11 to 30 carbon atoms. The fluorination may be carried out by known means; the exact composition of the resulting products is not precisely known.

SUMMARY OF THE INVENTION

The highly fluorinated hydrocarbons obtained from the fluorination of alkyladamantanes may be produced in accordance with this invention, by known means, as for example by a process comprising contacting an alkyladamantane hydrocarbon, in vapor phase, with a fluoride of a transition metal (e.g., $MnF_3$, $AgF_2$, $CoF_3$) at 200°–400° C. One preferred class of adamantane hydrocarbons contains in the range of 12 to 14 carbon atoms and contains methyl and/or ethyl groups.

This invention relates especially to highly fluorinated hydrocarbons, including perfluorinated compounds having 11–30 (more preferred especially 12–14) carbon atoms per molecule. Alkyladamantanes from which the fluorinated products can be derived include 1,3-dimethyladamantane, 1,3,5-trimethyladamantane, 1-ethyladamantane, 1-methyladamantane, 1-ethyl-3-methyladamantane and 1-ethyl-3,5-dimethyladamantane. The preferred fluorinated products of the invention are liquids at room temperature and are characterized by a high degree of stability and an unusually wide temperature range on which they remain in liquid state.

The carbon nucleus of adamantane starting material (tricyclo-3.3.1.1$^{3,7}$ decane) contains ten carbon atoms arranged in a completely symmetrical, strainless manner such that four of the carbon atoms occupy bridgehead positions. The structure of adamantane ($C_{10}H_{16}$) is commonly depicted structurally as follows:

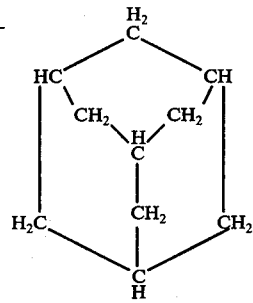

This hydrocarbon has a melting point of 268° C., sublimes beneath its melting point and hence does not occur in liquid form.

The starting hydrocarbons for preparing the fluorinated products of the present invention are $C_{11}$–$C_{30}$ alkyladamantanes, for example, $C_{12}$–$C_{14}$ alkyl derivative of adamantane having from one to four alkyl groups, which groups are methyl and/or ethyl and contain a total of from two to four alkyl carbon atoms. The alkyl substituents are preferably positioned at bridgehead carbon atoms. Thus the starting hydrocarbon in the $C_{12}$–$C_{14}$ group includes 1,3-dimethyladamantane, 1,3,5-trimethyladamantane, 1-ethyladamantane, 1,3,5,7-tetramethyladamantane. Unlike adamantane itself, most alkyl derivatives are liquids even at temperatures considerably below 0° C.

According to the invention, these alkyladamantanes are subjected to fluorinating conditions effective to result in fluorination or perfluorination of the hydrocarbons, typically to a degree of fluorination which is at least 75% of that corresponding to perfluorination. In other words at least 75% of the hydrogen atoms, more preferably at least 90% thereof, and most preferably 100% are replaced by fluorine atoms. Thus the products from dimethyladamantane and ethyladamantane ($C_{12}H_{20}$) contain an average of at least 15 fluorine atoms, those from trimethyladamantane and ethylmethyladamantane ($C_{13}H_{22}$) contain at least 17 fluorine atoms and that from ethyldimethyladamantane ($C_{14}H_{24}$) contain at least 18 fluorine atoms. In cases where the product is to be used as a dielectric medium, for example, as a dielectric coolant for transformers, or for biomedical applications, fluorinating conditions are used such that all of the hydrogen atoms are replaced by fluorine atoms. This results in a product having a low dielectric constant and low power factor, and low toxicity. In traction fluid blends with napthene or hydrogenated polyolefin oils, a product having a lower degree of fluorination can be useful for solubility properties.

The preferred highly fluorinated hyrocarbons of the invention are liquids at temperatures even below $-25°$ C. and they have boiling points above 170° C. Thus they remain in liquid state throughout an unusually wide temperature range. They are resistant to strong acids and alkalis, oxidizing and reducing agents, and are further characterized by high density, immiscibility with hydrocarbons or with water, non-corrosiveness and non-flammability. These properties make the products especially suitable for use as hydraulic fluids and dielectric coolants. The following are some of the applications for which the highly fluorinated and perfluorinated hydrocarbons are particularly useful: organ perfusion media, artificial blood, automotive brake fluids, gas turbine engine coolant, arc quenching fluid, instrument fluid and dielectric coolant for transformers, electronic assemblies, power tubes, generators, motors, limited slip differential, traction or friction drive, roller clutch, roller bearings and the like. As automotive brake fluids the fluorinated $C_{12}$-$C_{14}$ adamantanes containing ethyl and/or methyl substituents provide reduced tendency to "fade out", and, due to their tractive properties, provide less danger if fluid leaks on to the brake drums.

Fluorination of the alkyladamantanes can be carried out according to known methods for fluorinating hydrocarbons. The preferred method involves contacting the alkyladamantane in vapor form at a temperature in the range of 200°–400° C. with a bed of powdered cobaltic fluoride ($CoF_3$). In this procedure the $CoF_3$ reacts with the hydrocarbon forming HF and substituting fluorine in place of the hydrogen on both the adamantane nucleus and the alkyl substituents. This fluorinating procedure (for hydrocarbons) has been described in Stacey, "Advances in Fluorine Chemistry", Vol. I, (1961), pages 166 et seq. Sufficient contacting of the hydrocarbon with $CoF_3$ is carried out to provide at least 75%, more preferably 90% of the hydrogen atoms to be replaced by fluorine atoms. If necessary, partly fluorinated effluent from the reactor can be recycled for further fluorination. In cases where the product is to be used as a dielectric medium, or other uses where perfluorinated materials are desirable, e.g., biomedical applications, contacting with the $CoF_3$ should be sufficiently prolonged to effect perfluorination, i.e., complete replacement of all hydrogen atoms by fluorine. When this is done, some of the products which can be obtained include perfluoro-1,3-dimethyladamantane, perfluoro-1,3,5-trimethyladamantane, perfluoro-1-ethyladamantane, perfluoro-1-ethyl-3-methyladamantane or perfluoro-1-ethyl-3,5-dimethyladamantane depending upon which hydrocarbon is used as feed.

Fluorination of the alkyladamantanes can also be effected by a less preferred process comprising electrolysis of an emulsion of the hydrocarbon in anhydrous hydrogen fluoride containing alkali metal fluoride or $H_2O$ as electrolyte. This type of fluorination is also described in the above-mentioned text. Vol. I, pages 129–138. The electrolysis can be carried out at a temperature of 0°–10° C. using a potential of about 5V.

The $C_{12}$-$C_{14}$ alkyladamantanes to be fluorinated can be obtained by the isomerization of $C_{12}$-$C_{14}$ perhydroaromatic hydrocarbons containing three rings using HF—$BF_3$ or aluminum chloride or bromide as catalyst. Schneider U.S. Pat. No. 3,128,316 describes isomerizations of this type using aluminum halide catalysts. By way of example, perhydroacenaphthene which has 12 carbon atoms and 3 rings can be isomerized by means of HF—$BF_3$ or $AlCl_3$—HCl to 1-ethyladamantane. Actually this compound is an intermediate in the isomerization reaction, and if the reaction is allowed to proceed far enough the end product will be 1,3-dimethyladamantane. Hence, in cases where 1-ethyladamantane is the hydrocarbon for practicing the invention, it is important that the isomerization reaction be stopped at the proper point. When 1,3-dimethyladamantane is the desired hydrocarbon, the isomerization reaction should be allowed to proceed to substantial completion. The 1,3-dimethyladamantane or the 1-ethyladamantane can be produced in this manner from any tricyclic naphthene having 12 carbon atoms per molecule. Our U.S. Pat. No. 3,597,358 describes further methods of obtaining such alkyladamantanes.

Certain preferred fluorinated products of the process of the present invention have approximately the freezing and boiling characteristics shown in Table 1.

TABLE 1

| Parent Hydrocarbon | Freezing Point ° C. | Boiling Range ° C. |
| --- | --- | --- |
| 1-ethyladamantane | −55 | 178–205 |
| 1-ethyl-3-methyladamantane | −80 | 180–207 |
| 1-ethyl-3,5-dimethyladamantane | −80 | 185–210 |
| 1,3-dimethyladamantane | −30 | 173–201 |
| 1,3,5-trimethyladamantane | −70 | 183–208 |

The boiling ranges shown are typical for products which are not completely fluorinated. The perfluorinated products do not boil over a substantial range. From the data given it can be seen that fluorinated products of the invention can have an unusually large liquid range and hence can be used in applications where either very low or relatively high temperatures are encountered.

ILLUSTRATIVE EXAMPLES

EXAMPLE 1

Acenaphthene is dissolved in methylcyclohexane and then hydrogenated at 475° F. and under a hydrogen pressure of 500 p.s.i.g. using a 1% platinum-on-alumina catalyst to form perhydroacenaphthene ($C_{12}H_{20}$). After removal of most of the methylcyclohexane by distillation, the perhydroacenaphthene containing 3.3% of residual methylcyclohexane is charged in amount of 520 g. to an autoclave provided with means for effecting agitation. 70 g. of anhydrous HF are added, 30 g. of $BF_3$ are pressured into the autoclave and the mixture is heated to and maintained in the range of 60°–100° C. and mainly in the neighborhood of 95° C. for 6.3 hours while being agitated. The reaction is then stopped, and the hydrocarbon layer is separated from the catalyst layer and washed to remove residual catalyst. Analysis of the hydrocarbon produce by vapor phase chromatography gives the results shown in Table 2.

TABLE 2

| | Charge | Product |
|---|---|---|
| Methylcyclohexane | 3.3% | — |
| Isodecalins | — | 0.6% |
| 1,3-dimethyladamantane | — | 20.1 |
| Non-abridged dimethyl-adamantane | — | 15.5 |
| 1-ethyladamantane | — | 48.9 |
| Perhydroacenaphthene | 96.7 | — |
| Perhydroacenaphthene & 2-ethyladamantane | — | 14.9 |
| | 100% | 100% |

The data in Table 2 show that 1-ethyladamantane is the main product when the isomerization is carried out under the conditions described. The portion of effluent from the chromaograph containing the ethyladamantane is collected separately and 1-ethyladamantane of substantially 100% purity is obtained.

The 1-ethyladamantane is then fluorinated by vaporizing 15 ml. of it and passing the vapor along with a slow stream of nitrogen over a 700 g. bed of $CoF_3$ in a horizontal, stirred tubular reactor maintained at from 250–350° C. The reaction product is collected in a receiver cooled by dry ice. The collected material is then washed with water and dilute caustic to remove HF and dried. Elemental analysis of the product is as follows:

| % C | 27.5% |
|---|---|
| % H | Trace |
| % F | 72.5% |

These data show that the product is substantially completely fluorinated. It has a freezing point of about −55° C. and a boiling point of about 190° C.

EXAMPLE 2

Perhydroanthracene is prepared by hydrogenating anthracene by the procedure used in the preceding example. A 617 g. mixture of 83.4% perhydroanthracene and 16.6% methylcyclohexane is isomerized using 85 g. of HF and 35 g. of $BF_3$ as catalyst. The reaction is carried out for 66 hours at about 90° C. The hydrocarbon product has the composition in Table 3 as determined by vapor phase chromatography.

TABLE 3

| | Charge | Product |
|---|---|---|
| $C_4$–$C_7$ paraffins | — | 2.4 |
| Methylcyclohexane | 16.6 | 1.7 |
| Isodecalins | — | 1.7 |
| 1,3,5,7-tetramethyladamantane | — | 19.2 |
| 1-ethyl-3,5-dimethyladamantane | — | 50.0 |
| Perhydroanthracenes | 83.4 | 25.0 |

The data is Table 3 show that 1-ethyl-3,5-dimethyladamantane is a major product. The effluent from the chromatograph that contained this compound is collected separately and substantially pure 1-ethyl-3,5-dimethyladamantane is thereby obtained. Disappearance of the methylcyclohexane in this run can be accounted for largely by cracking, which forms light hydrocarbons that are lost through vaporization.

The 1-ethyl-3,5-dimethyladamantane is fluorinated by means of $CoF_3$ under conditions similar to those described in Example 1. Elemental analysis of the fluorinated product is as follows:

| C | 29.4% |
|---|---|
| F | 69.7% |
| H | 0.5% |

These results correspond approximately to the empirical formula $C_{14}F_{21}H_3$, thus indicating that an average of about three hydrogen atoms per molecule remains in the product. Complete perfluorination can be achieved by subjecting the fluorinated material to further reaction in the presence of $CoF_3$.

The fluorinated product ($C_{14}F_{21}H_3$) is found to have the properties listed in Table 4.

TABLE 4

| Properties of $C_{14}F_{21}H_3$ | |
|---|---|
| Physical State at 25° C. | Colorless liquid |
| Odor | None |
| Boiling Range | 185–210° C. |
| Freezing Point | −80° C. |
| Density at 20° C. | 1.8914 |
| Refractive Index at 20° C. | 1.3100 |
| Dielectric Constant | 3.21 |
| Power Factor | 0.09 |

These data indicate that the product is particularly useful as a hydraulic fluid for either low temperature or relatively high temperature applications. The dielectric constant and power factor are generally higher than would be desired for electrical application. This is due to the presence of hydrogen atoms, and hence these values can be reduced by more complete fluorination of the product. The completely perfluorinated product has a boiling point in the neighborhood of 210° C.

EXAMPLE 3

Fluorene is hydrogenated under the conditions similar to those of Example 1. This produces perhydrofluorene ($C_{13}H_{22}$). Isomerization of the latter under conditions similar to those described in Example 2 results in a good yield of 1-ethyl-3-methyladamantane which is separately collected from the chromatograph effluent. Fluorination of this compound under conditions as in Example 1 except using 500 g. of $CoF_3$ yields a highly fluorinated product averaging 1–2 hydrogen atoms per molecule. This product is a colorless, odorless, liquid at room temperature. It has a freezing point of less than −80° C. and a boiling range of about 195°–215° C. Elemental analysis shows that the product contains an average of 1–2 hydrogen atoms per molecule. The product can be further treated with $CoF_3$ to effect complete fluorination and yield perfluorinated product having a boiling point of about 207° C.

When the fluorination is done by electrolysis of the alkyladamantanes in HF, substantially the same fluorinated products can be obtained.

Some of the fluorinated hydrocarbons of this invention are useful as lubricants or components of lubricants for a power transmission system comprising a friction drive transmission and, as a lubricant therefor, a composition comprising base stock having a kinematic viscosity at 210° F. in the range of 1.5–200.0 cs., said base stock comprising at least one $C_{10}$–$C_{40}$ saturated fluorinated adamantane compound, said adamantane compound containing no elements other than carbon, hydrogen and fluorine.

The preferred saturated fluorinated adamantane compounds are obtained by substitution of fluorine for some or all of the hydrogen in the following compounds: derivatives of alkyl admantanes, perhydrogenated derivatives of adamantanes, alkyl derivatives of the members of the above listed groups wherein the alkyl group contains from 1–10 carbon atoms, cycloalkyl derivatives of the above-noted groups, wherein the cycloalkyl group is cyclopentane, cyclohexane, or a mono- or dimethyl derivative of cyclopentane or cyclohexane, a dicycloalkyl derivative of adamantane wherein the dicycloalkyl group is dicyclohexane, di(cyclohexyl) propane, or a mono-, di-, or tetramethyl derivative thereof, an alkyl derivative of adamantane, preferably wherein the alkyl group contains from 1–10 carbon atoms, adamantane containing as substituents both alkyl and cycloalkyl groups, wherein the alkyl group contains from 1–10 carbon atoms, and the cycloalkyl group is cyclopentane, cyclohexane or an alkyl derivative thereof.

An example of a preferred saturated cycloalkyl adamantane compound is perhydro-1-alkyl adamantane (prepared by perhydrogenation of 1-alkyl adamantane, using Raney nickel catalyst at 200° C. and 3000 p.s.i. of $H_2$), which can be fluorinated by the process of the present invention.

Other useful tractants are products obtained by fluorination by the present process of alkylated adamantane hydrocarbons of the $C_{10}$–$C_{30}$ range having 1–4 open bridgehead positions. For example, the products obtained by the alkylation reaction of U.S. Pat. No. 3,382,288, issued May 7, 1968 to Abraham Schneider.

In general fluoro and perfluoro derivatives of any of the above adamantane compounds, such as are obtained by passing the admantane compound in vapor phase over a bed of $CoF_3$ in a tubular, stirred reactor maintained at about 200°–400° C. are useful as traction fluids, or components of traction fluids.

Another utility for such fluorinated and perfluorinated derivatives is as a functional fluid (i.e., heat transfer agent) or lubricant in a Rankin cycle engine. In general, the man skilled in this art can choose such a lubricant or functional fluid from the thermodynamic properties thereof. These properties can be obtained by experiment and/or by calculation. Another utility is in brake fluids with reduced fade-out.

Especially preferred adamantane compounds are obtained by fluorination of di-methylbutyl-adamantane, dimethyloctyladamantane, dimethylcyclopentayladamantane, dimethylcyclohexyladamantane, dicyclohexylethyladamantane, and wherein all of the substituents on the admantane are at bridgehead position.

Another preferred tractant comprises a fluorinated or perfluorinated mixture of substitued adamantanes derived by contacting a petroleum hydrocarbon stream which is substantially free from aromatic or olefinic unsaturation and which contains at least one perhydroaromatic hydrocarbon having three rings and at least 12 carbon atoms at a temperature in the range of −5° to +50° C. with an aluminum halide catalyst, and continuing such contact until at least a substantial proportion of the perhydroaromatic has been converted to hydrocarbon product having adamantane structure. Prior to fluorination by the present process the adamantanes so produced can be further converted by alkylation, as by the method of the aforementioned Schneider patent application.

Due to their high coefficient of traction, compared with their viscosity index, the fluorinated adamantane derivatives are especially useful components for blending with other fluorinated compounds or with naphthenes, with branched paraffins, and with fluorinated or hydrogenated naphthenic of paraffinic petroleum oils in the compounding of traction fluids (or other functional fluids).

The invention claimed is:

1. Highly fluorinated hydrocarbons formed by fluorinating an alkyladamantane having from 11 to 30 carbon atoms in which the degree of fluorination is at least 75% of that corresponding to perfluorination.

2. The product of claim 1 derived from one of the following: dimethylbutyladamantane, dimethyloctyladamantane, dicyclohexylethyladamantane, dimethylcyclopentyladamantane, or dimethylcyclohexyladamantane, wherein all of the substituents on the adamantane are at bridgehead positions.

3. The product of claim 1 which is perfluorinated.

4. The product of claim 2 which is perfluorinated.

5. The product of claim 1 in which the degree of fluorination is at least 90% of that corresponding to perfluorination.